(12) United States Patent
Kaushik et al.

(10) Patent No.: US 8,951,581 B2
(45) Date of Patent: *Feb. 10, 2015

(54) **BIOACTIVE WATER FRACTION FROM *GOMPHOSTEMA NIVEUM***

(75) Inventors: Mahabir Prashad Kaushik, Pradesh (IN); Duraipandian Thavaselvam, Pradesh (IN); Manisha Nivsarkar, Pradesh (IN); Sanjay Kumar, Pradesh (IN); Krishnamurthy Sekhar, Pradesh (IN); Hemant Kumar Gogoi, Assam (IN); Deba Koch, Assam (IN)

(73) Assignee: The Director General, Defence Research and Development Organisation, New Delhi (IN)

( * ) Notice: Subject to any disclaimer, the term of this patent is extended or adjusted under 35 U.S.C. 154(b) by 334 days.

This patent is subject to a terminal disclaimer.

(21) Appl. No.: 13/400,921

(22) Filed: Feb. 21, 2012

(65) Prior Publication Data

US 2013/0052287 A1    Feb. 28, 2013

Related U.S. Application Data

(62) Division of application No. 11/992,927, filed as application No. PCT/IN2006/000318 on Aug. 30, 2006, now Pat. No. 8,282,968.

(30) Foreign Application Priority Data

Oct. 4, 2005 (IN) .......................... 2073-DEL-2004

(51) Int. Cl.
   *A01N 65/00*    (2009.01)
   *A61K 36/53*    (2006.01)
(52) U.S. Cl.
   CPC ..................................... *A61K 36/53* (2013.01)
   USPC .......................................................... 424/725

(58) Field of Classification Search
   CPC .............. A61K 36/00; A61K 2236/00; A61K 2236/33; A61K 2236/35; A61K 2236/37; A61K 2236/55
   USPC .................................................. 424/725, 774
   See application file for complete search history.

(56) References Cited

PUBLICATIONS

Klayman, Dalniel L., "Qinghaosu (Artemisinin): An Antimalarial Drug from China", Science, americal Associationfor the advancement of Science, vol. 228, May 31, 1985, pp. 1049-1055.
Dutta, M. L., et al., Ethno-medico botany of the Deories of Assam, India, Fitoterapia, vol. 59, No. 2, 1998, pp. 147-154.
Singh, V. K., et al., Folk medicines in primary health care: common plants used for treatment of fevers in India, Fitoterapia, vol. 65, No. 1, 1994, pp. 68-74.
Alemmeren, Jamir S., "Vascular plant diversity in the sacred groves of Jaintia Hills in northeast India", Bioversity and Conservation, vol. 12, No. 7, Jul. 2003, pp. 1497-1510.
Singh, K.K., et al., "Role of ethnoherbals in bio-prospecting of safe phytomedicines and nutraceuticals for the 21$^{st}$ century", Journal of Medicinal and Aromatic Plant Sciences, Proceedings of the National Seminar on the Frontiers of Research and Development in Medicinal Plants, Sep. 15-18, 2000, pp. 579-596.
Bhakuni, D. S., et al., Screening of Indian plants for biological activity: Part XIV, Indian Journal of Experimental Biology, vol. 28, No. 7, 1990, pp. 619-637.
Deka, H., et al., In Vitro Evaluation of Antimicrobial Properties of Two Species of Genus *Gomphostemma*, Journal of Cell and Tissue Research, vol. 6, No. 2, 2006, Abstract.

*Primary Examiner* — Michael Meller
(74) *Attorney, Agent, or Firm* — Ladas & Parry LLP

(57) ABSTRACT

The present invention relates to a novel bioactive water fraction obtained from the leaves of an herb named *Gomphostema niveum* commonly found in North Eastern part of India, and which is useful for inhibiting the growth of malarial parasite *Plasmodium falciparum*. The present invention also relates to a method for the extraction of said bioactive fraction. The present invention also provides methods for treatment of malaria using such bioactive water fractions and use of such bioactive water fractions for the treatment of malaria.

1 Claim, 2 Drawing Sheets

BIOACTIVE WATER FRACTION FROM *GOMPHOSTEMA NIVEUM*

This application is a divisional of application Ser. No. 11/992,927 filed on Apr. 1, 2010 now U.S. Pat. No. 8,282,968, which is a 371 of International Application PCT/IN2006/000318 filed on Aug. 30, 2006, and entitled "BIOACTIVE WATER FRACTION FROM *GOMPHOSTEMA NIVEUM*" which as published in the English language on 12 Apr. 2007, with International Publication Number WO 2007/039916 A2 and which claims priority from Indian Patent Application 2073-DEL-2004, filed 4 Oct. 2005, claims the benefit thereof and incorporates the same by reference.

FIELD OF INVENTION

The present invention relates to a novel bioactive water fraction obtained from the leaves of an herb name *Gotnphostema niveunm* commonly found in North Eastern part of India, and which is useful for inhibiting the growth of malarial parasite *Plasmodium falciparum*. The present invention also relates to a method for the extraction of said bioactive fraction. The present invention also provides methods for treatment of malaria using such bioactive water fractions and use of such bioactive water fractions for the treatment of malaria.

BACKGROUND OF THE INVENTION AND PRIOR ART

Malaria is the most prevalent among the insect borne disease accounting for more than two million deaths out of 400 million cases reported each year (Greenwood et. al., *Nature* 9415), 670(2002)) caused by *Plasmodium falciparum*. (Depote et al. *Trends in parasitology* (20), 4, 165-198, (2004)). More than half of the world's population lives in areas where they remain at risk of malarial infection (Sachs et al *Nature*, (415), 686 (2002). The derivation of important anti-malarial compound started with the discovery of cinchona bark powder (quinine) (Brooking, GB 106430, (1917)) in 1820. Subsequently post World War-I was a period of intense work in maintaining such ethnobotanical records in which the use of quinine has remained the drug of choice of malaria. In 1940 another anti-malarial drug chloroquine (Ringwald et al, *Bulletin of the world health organization*, 77(1), 34, (1999)) was synthesized and until recently this was the only drug used for the treatment of malaria. Unfortunately, after an early success, the malarial parasite especially *P. falciparum* became resistant to chloroquine. Treatment of chloroquine resistant malaria (White et al. Delaying anti-malarial drug resistance with combination chemotherapy *Parasitologia*, (41), 301-308, (1999)) was done with alternative drug or drug combination (Tulp et. al, *Drug discovery today* (9)450, (2004)) which are rather expensive and sometimes toxic. Furthermore, these combinations are not always dependent upon pharmacokinetic principle due to inadequate knowledge of metabolism and mechanism of action of most anti-malarial drugs. In the last few years a plant based anti-malarial drug isolated from the Chinese plant *Artiinisinin anima* (Klayman, Science (228),1049,(1985)), Bharel et al. *Fitoterapia*, (67), 387-399, (1996)) proved to be very active against *P. falciparum*. However, the use of Artemisinin, an endoperoxide sesquiterpene lactone is somewhat limited because of its relatively high cost, limited production of GMP standards and reports of toxicity (Haynes et al. *Curr. Opin. Infect. Dis*, (14), 719-726, (2001)). The current route for the total synthesis of Artemisinin (Qinghaosu) (U.S. Pat. No. 6,710,074 (2004) is too complex for commercial production (Schmid et at *J. Am. Chem. Soc.* (105), 624-625, (1983). It is currently prepared by large scale extraction from *Artemisia annua* (sweet warwood) and derivative such as artemether, artesunate, arteether and dihydroartemisinin are prepared semi synthetically from the purified extract. Moreover, difficulties have also been encountered in the production of high quality material (Haynes et al. *Curr. Opin. Infect. Dis*., (14), 719-726, (2001)).

Thus, the widespread resistance of malarial parasite to the majority of drugs, necessitates the development of new drug (Wiesner et al. *Angew. Chem. Int. Ed.* (42), 5274-5293, (2003)) which should be structurally different from classical compounds with novel mechanism of action to overcome the resistance problem. Recently Ihara et, al disclosed about compounds having anti-malarial activity (U.S. Pat. No. 6,710,074 (2002)) from synthesis. In recent past different classes of compound are also reported having anti-malarial activity like substituted 1,2,4 trioxane (U.S. Pat. No. 6,737,438(2002)), flavonoids (WO2004000306 (2003)), naphthylisoquinoline (U.S. Pat. No. 6,627,641(2003)), indoloquinazoles (U.S. Pat. No. 6,531,487(2003)), trioxolanes (U.S. Pat. No. 6,486,199(2002)), betacarboline alkaloids (U.S. Pat. No. 6,143,756(2000)), vocamine (WO 9948501 (1999)), acetyl glucosamine derivatives (DE3220426(1983)) and so on. Recently many patents like U.S. Pat. No. 6,710,074, WO2004000319, U.S. Pat. No. 5,264,726, US2003212098, WO2004000306, EP1076057, WO9948501, U.S. Pat. Nos. 5,290,553, 6,143,756 and 6,627,641 disclosed compounds having anti *Plasmodium falciparum* activity from natural origin mainly plants. Hence the ethnopharmacologial approach for the search of new anti-malarial has proved to be more predictive.

As a part of ongoing research programmes on bioresources, we have screened large number of plants from the north eastern region for the anti-malarial inhibition studies. Plant selection was mainly based on various criteria such as chemotaxonomic data, field observation and random collection.

Malaria is caused by protozoa of the genus *Plasmodium*. Because of its prevalence, virulence and drug resistance, it is the most serious and widespread parasitic disease encountered by mankind. The inadequate armory of drugs in widespread use for the treatment of malaria and lack of affordable new drugs are the limiting factors in the fight against malaria, which underscores the continuing need of research for development of new drugs.

There is therefore a need to develop new active compounds as an alternative to chloroquine and especially from artemisinin, a plant based anti-malarial drug isolated from the Chinese plant *Artemisia annua*. The urgent need is to investigate the natural source with new ethanophramacological approach for the search of new anti-malarial especially from the North Eastern part of India, which has not been screened so far. Another need is to develop suitable method for the extraction, isolation and identification of bioactive principles form the plant extract having the anti-malarial properties. The recently developed new isolation and characterization techniques together with development of new pharmacological testing have led to interest in plants as a source of new drugs. However, a promising approach is needed to use these agents as templates for designing new derivatives with improve properties.

Objects of the Present Invention

The main objective of the invention is to develop a novel anti-malarial agent inhibiting the growth of chloroquine resistant and chloroquine sensitive malarial parasite from the natural source.

Another objective of the invention is to investigate the anti-malarial properties of Indian medicinal plant from the North Eastern region of India for the treatment of malaria (selection of the plant is based on chemotaxonomic data).

More particular objective is to develop a simple and efficient method for the extraction, isolation and identification of the active components from the Indian medicinal plants.

Yet another objective is to perform in vitro bioassay of crude extracts against the growth of malarial parasite.

Further objective of the invention is to develop a reproducible fingerprinting HPLC method for the routine monitoring of the crude extract.

Still another objective of the invention is to provide a suitable technique for the identification, evaluation and monitoring of in vitro anti-malarial activity.

Another objective of the invention is to perform the temperature stability studies for the different crude extract, this will be helpful for the storage of bioactive fraction.

Yet another objective is to evaluate the various routes of administration and to establish their stability in body fluids, toxicity and capacity to reach infected tissue in an adequate concentration during in vivo analysis.

Statement of Invention

The present invention therefore provides a novel bioactive water fraction obtained from the leaves of *Gomphostema nivewn*.

The present invention also provides a method for the preparation of a novel bioactive fraction from *Gomphostema niveum* comprising air drying leaves of the plant, powdering the air dried leaves and subjecting the powder to extraction with water filtering the extract and concentrating to dryness under reduced fraction to obtain the bioactive water extract.

In one embodiment of the invention, water extraction is carried out three times.

In another embodiment of the invention, extraction is carried out by Soxhlet extraction method at reflux temperature for eight hours.

In yet another embodiment of the invention, extraction is carried out using triple distilled water.

In yet another embodiment of the invention, the filtered extract is concentrated to dryness under reduced pressure of about 86 psi at a temperature of about 46° C. using a rotary evaporator.

In another embodiment of the invention, the water extract obtained is further fractionated by liquid-liquid extraction using solvents selected from the group consisting of hexane, diethyl ether, chloroform and ethanol on the basis of increasing polarity, the extracts then being concentrated to dryness under reduced pressure of about 150 psi and at a temperature of about 30° C.

The present invention also provides a pharmaceutical composition for the treatment of malaria comprising a bioactive water extract of Gomphostema niveum and one or more pharmaceutically acceptable additives.

In one embodiment of the invention, the pharmaceutically acceptable additives are selected from the group consisting of carriers diluents, stabilizing agents, solvents, flavoring agents and the like.

BRIEF DESCRIPTION OF THE ACCOMPANYING DRAWINGS

DETAILED DESCRIPTION OF THE INVENTION

Figure 1:
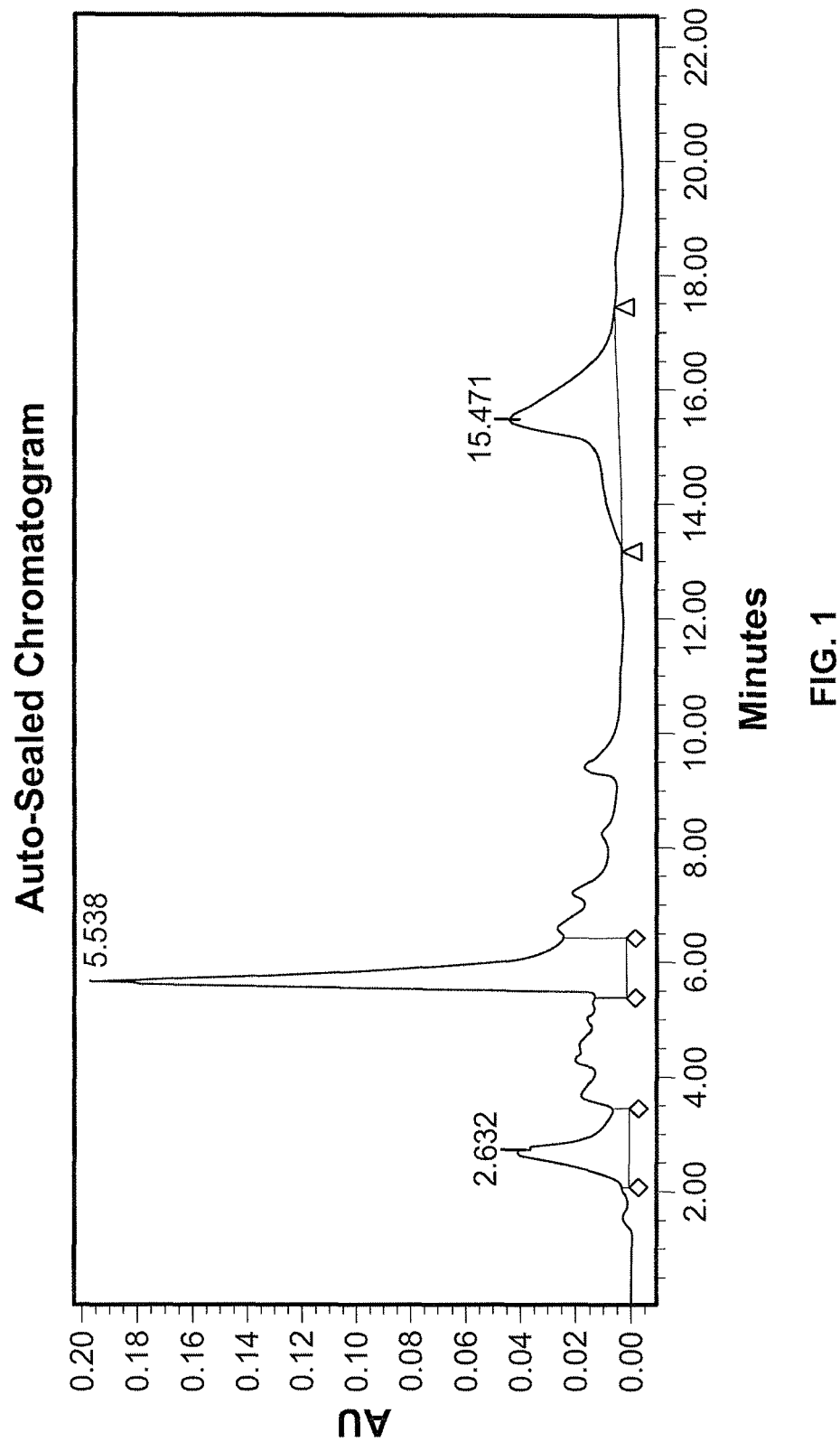
FIG. 1 is the HPLC profile of the crude extract of the invention.
Figure 2:
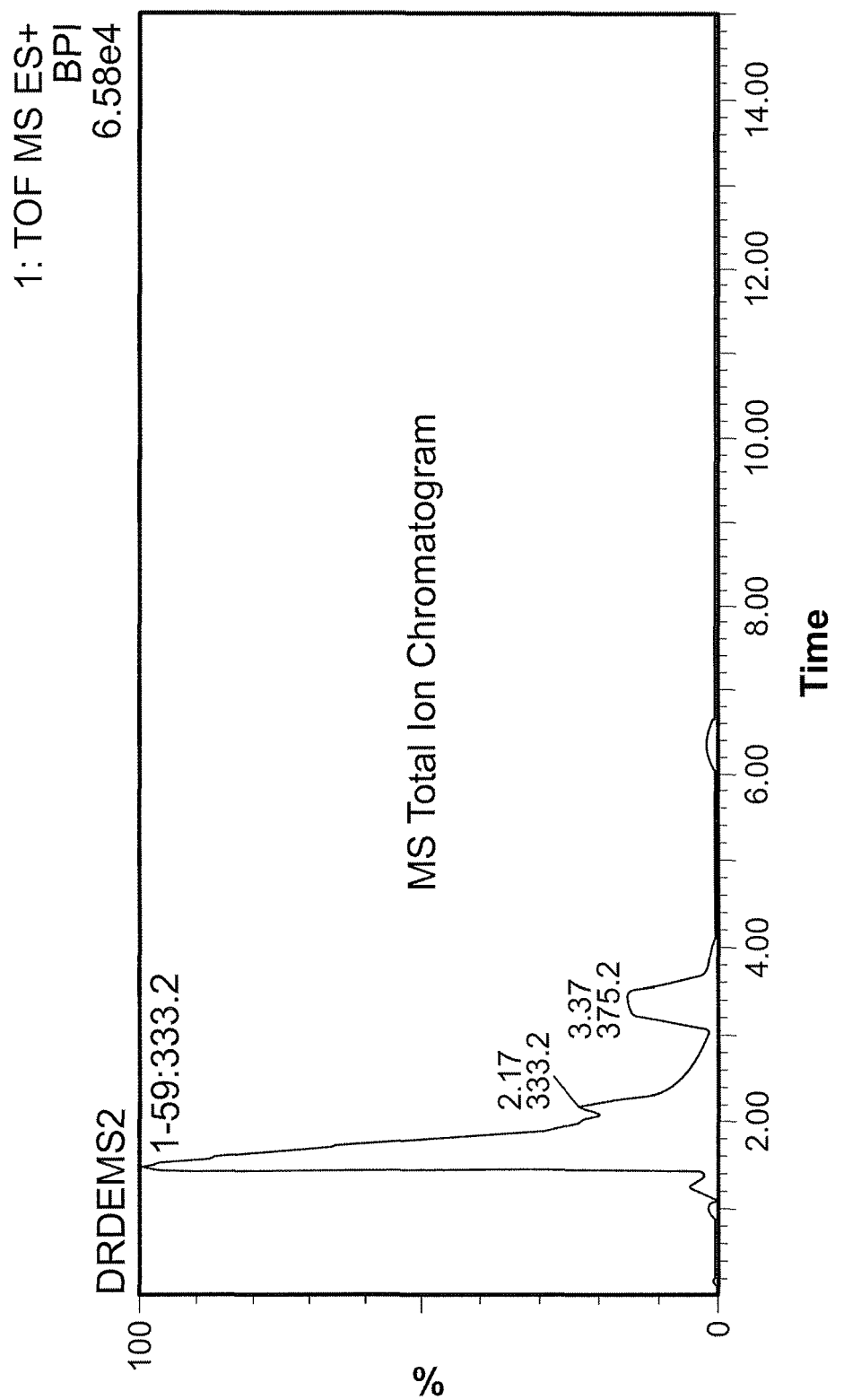
FIG. 2 is the total ion chromatogram of the crude extract after further fractionation.

The increasing resistance of *Plasmodium falciparum* to currently available drug such as choloroquine, present a challenge in the treatment of malaria, which still remains one of the treatment for malaria, which still remains one of the leading causes of death in the world. Consequently new agents are urgently needed to treat the organism.

The present invention provides a bioactive water fraction named as GN-W obtained from the leaves of plant *Gomphostema niveum* having inhibitory activity against chloroquine resistant and chloroquine sensitive malarial parasite. According to another embodiment of the present invention it provides the simple and efficient method of extraction, isolation and identification for the bioactive compound from the sun/air dried leaves of *Gomphostema niveum* is provided.

Further in accordance with another embodiment of the present invention is the development of fingerprinting high performance liquid chromatographic (HPLC) method for the routine monitoring of the crude extract. Additionally this invention provides a suitable technique for in vitro and in vivo bio-evaluation of crude extract.

Yet another embodiment of the present invention, synergistic effect has also been investigated in case of in vitro and in vivo anti-malarial bioassay of the crude extract. This invention also presents the solubility and temperature related stability studies for the bioactive fraction. Evaluation of various routes of administration their stability in body fluid, toxicity, capacity to reach infected tissue in an adequate concentration during in vitro bioassay has also been described by the present invention. Hence the present invention provides a pharmaceutical formulation named as GN-W which exhibit excellent anti-malarial activity.

Although the invention has been described in detail with reference to a preferred embodiment it is to be understood that the above description of the present invention is susceptible to considerable modifications, variations and adaptations by those skilled in the art, such intended to be considered to be within the scope and spirit of the present invention.

The detailed description of the invention which provides a bioactive water fraction named as GN-W obtained from the plant Gomphostema niveum having inhibitory activity against chloroquine resistant and chloroquine sensitive malarial parasite.

The process of the bioactive water fraction is now shown with an example, which is illustrative and is not intended to be taken restrictively to imply any limitation on the scope of the present invention.

The process comprised of the following steps:

Step 1

In our efforts to isolate and identify more potent naturally occurring compounds which are active against chloroquine resistant malarial parasite, we carry out a systematic bio-guided fractionation of the water extract prepared from the leaves of Indian medicinal plant *Gomphostema niveum*. Plant material (leaves) is collected in the month of June and September from Dhemaji Assam located in the North Eastern part of India with the help of Defence Research Laboratory, Texpur. Leaves are dried in shade for forty eight hours and ground to fine powder.

Step 2

Extract the 100 gm of dry leaves with 500 ml of triple distilled water using soxhlet extraction method at reflux temperature (100° C.) for eight hours. Three repeated extractions are carried out by using 500 ml of triple distilled water respectively. The extracts are then filtered, pooled together and concentrated to dryness under reduced pressure (at 86 psi and 46° C.) using the rotary evaporator. Concentrated fraction named as GN-W (25 gm).

Step 3,

The water extract GN-W (25 gm) is further fractionated by liquid—liquid extraction using different solvents like hexane (200 ml), diethyl ether (200 ml), chloroform (200 ml) and ethanol (200 ml) on the basis of their increasing polarity. All the extracts are pooled together separately and concentrated to dryness under reduced pressure (150 psi and 30° C.) and named as GN-E (10 gms), GN-C (2 gm) and GN-ET (6 gm). All these fractions are tested against inhibition studies of malarial parasite. The result indicates that the ether/chloroform fraction exhibits maximum bioactivity against the malarial parasite. The percentage inhibition for ether/chloroform fraction is 86-90%. An interesting feature can be observed that the ethanolic fraction does not inhibit the growth of malarial parasite. Hence we hypothesize that the ether extract might contain some active principles which are able to inhibit the growth of malarial parasite. Therefore, to isolate the biologically active principle column chromatography is carried out for the ether/chloroform fraction (GN-E). The list of extracts prepared and the laboratory course are shown in table 1.

TABLE 1

| Plant Name and part | Solvent | Code |
|---|---|---|
| *Gomphostema niveum* Leaves | Water | GN-W |
|  | Hexane | GN-H |
|  | Diethyl ether | GN-E |
|  | Chloroform | GN-C |
|  | Ethanol | GN-ET |

Step 4

To purify the active principle from the ether/chloroform extract silica gel column chromatography is performed. Any person who is skilled in the art of related subjects can perform technique. About 10 g of ether fraction is packed on to a silica gel (100 gm), 200-400 mesh) column fractions are subsequently analyzed for their in vitro inhibitory activity against the *P. falciparum*. Result indicates that the column fractions elutes using 50-60% hexane in ethyl acetate is able to inhibit the malarial parasite and therefore process the ability to cure malaria. Amount of solvents use for the elution of different components from the ether fraction are as follows:- Hexane 100-500 ml (1-8 fractions), 10-20% ethyl acetate in hexane 25-50 ml (1-2 lit), 40-50% ethyl acetate in hexane 25-50 ml (1-2 lit) 50-60% ethyl acetate in hexane 25-50 ml (1.5-2.5 lit).

Step 5

Parallel extraction is also carry out by taking 50-60 gm of leaves using hexane (100-200 ml), diethyl ether/chloroform (100-200 ml), chloroform (100-200 ml) and ethyl alcohol (100-200 ml) at reflux temperature and also at room temperature for 8-10 hours. The extracts are then filtered, pooled together and concentrated to dryness under reduced pressure (at 150-200 psi and 30° C.) using the rotatory evaporator. Concentrated fractions are compared with respect to their HPLC profile and also evaluate in vitro.

Step 6

The separation of the constituents present in the extracts was carried out on Waters HPLC instrument with UV detector. A finger printing method was also developed for the routine monitoring of the crude extract. The HPLC conditions are as follows:

| | |
|---|---|
| Column: NOVAPAK C-18, 150 × 3.9 MM, 5 MICRON | Pump: water's LC-600 UV Detector: Water's 486 |
| Mobile phase: Acetonitrile: Water (60:40) | Reversed Phase Isocratic system Flow rate: 1 Ml/Min |
| Detectorλ: 254 NM | |

Step 7

Liquid Chromatography and mass spectrometric analysis of bioactive ether fraction (GN-E).

An aliquot of the sample is accurately weighed for dilution to a final analytical concentration of 100 μg/ml. In some cases however the entire content of unspecified quantity has to be reconstituted in 1 ml of appropriate solvent as specified in the sample submission details and diluted 100:1 for analysis.

LC Conditions (Isocratic)

Column: Waters Symmetry C18 2.1×100 mm

Mobile Phase: A=Water B=Acetonitrile

Gradient: Isocratic 60/40 A:B

Flowrate: 400 μl min split 4:1 into source

Injection Volume: 20 μl

U. V. Detector: Diode Array 220-300 nm (254 nm extracted)

LC Conditions (Gradient)

Column: Waters Symmetry C18 2.1×100 mm

Mobile Phase: A=Water+0.1% Formic Acid
  B=Acetonitrile+0.1% Formic Acid

Gradient: 5% to 95% B in 15 mins, hold to 20 mins then re-equilibrate to 5% B at 30 mins Flow rate: 400 μl min split 4:1 into source Injection Volume: 20 μl U. V. Detector: Diode Array 220-300 nm (254 nm extracted)

MS Conditions

Ion Mode: Electrospray +ve

Acquisition: 80-800Da at Ispectrum/sec, manual pusher at 35 μsec Real-time centroid exact mass mode.

Lockspray: Reference Mass (Sulfadimethoxine 311.0814 Da)

Resolution: 6, 000 FWHM Sampling Cone: 40V

Collision Gas: Argon

Collision Energy: MS Survey=5 eV (no fragmentation)

MSMS Conditions

Ion Mode: Electrospray +ve

Acquisition: 80-800Da at Ispectrum/sec, manual pusher at 35 μsec Real-time centroid exact mass mode.

Lockspray: Reference Mass (Sulfadimthoxine 311.0814 Da)

Resolution: 6, 000 FWHM Sampling Cone: 40 V Collision Gas:

Collision Energy: 10 eV to 40 eV (optimized for individual components)

Step 8

In Vitro Evaluation of Anti-Malarial Activity

Two strains of chloroquine sensitive strain and one strain of *P. falciparum* isolate from patients from Jagadalpur region of the country is adapted to and maintained in vitro. The cultures are maintained as per the standard culture procedures described earlier. The parasites are grown in O +ve human RBCs with the addition of RPMI 1640 culure media with 10% Himan serum as supplement. The cells are incubated at 37° C. at 5% $CO_2$ atmosphere and the parasitemia are checked after 24 hrs and media changed. When parasitemia exceeded 10% parasitized cells the cultured with the addition of fresh RBC. The parasite growth synchronizes by the sorbitol lysis method and synchronized ring stage parasites are used for testing. The in vitro testing is done in 100 μl complete media per well with the addition of 10 μl of erythrocytes with 2% of ring stages of parasites. All the tests are run in duplicates with in 96 well flat bottomed tissue culture plate and double dilutions are made for each of the test compound with individual control wells only with the RPMI 1640 and human serum supplement. The growth of the parasites in the presence of each of the test compound, Chloroquine and control wells are monitored by the examination of the giemsa stained blood smears made after 24 hrs of incubation. The counting is done for the presence of mature schizonts among 200 asexual parasites and the average schizont maturation inhibition is calculated by the formula $(1-N_t/N_c) \times 100$ where in $N_t$ and $N_c$ represent the number of schizont present in the test and control respectively. The IC 50, IC 90 and IC 99 values are calculated by using the commercial statistical package Sigmastat.

Invitro Antimalarial Inhibition Studies

| Compound | $IC_{50}$ | $IC_{90}$ |
|---|---|---|
| GN-W | 153.23 µg/ml | 752.29 µg/ml |
| GN-E | 103.53 µg/ml | 388.24 µg/ml |
| Chloroquine | 0.025 µM | 0.046 µM |

We claim:

1. A method for making an aqueous hexane, aqueous diethyl ether, aqueous chloroform or aqueous ethanol extract of *Gomphostema niveum* leaf comprising air drying leaves of *Gomphostema niveum* to produce air dried leaves of *Gomphostema niveum*, powdering the air dried leaves of *Gomphostema niveum* to produce powder of leaves of *Gomphostema niveum* and subjecting the powder of leaves of *Gomphostema niveum* to extraction with water at reflux temperature, filtering the extract of leaves of *Gomphostema niveum* to produce a water extract of *Gomphostema niveum*, further extracting the water extract of *Gomphostema niveum* by liquid-liquid extraction using solvents selected from the group consisting of hexane, diethyl ether, chloroform and ethanol on the basis of increasing polarity to produce an aqueous hexane, aqueous diethyl ether, aqueous chloroform or aqueous ethanol extract, then the aqueous hexane. aqueous diethyl ether, aqueous chloroform or aqueous ethanol extract is concentrated to dryness under reduced pressure of about 150 psi and at a temperature of about 30° C. to produce the aqueous hexanes aqueous diethyl ether, aqueous chloroform or aqueous ethanol extract of *Gomphostema niveum* leaf.

* * * * *